(12) United States Patent
Hu et al.

(10) Patent No.: US 8,530,590 B2
(45) Date of Patent: Sep. 10, 2013

(54) SOFT SILICONE MATERIALS FOR OPHTHALMIC APPLICATIONS

(75) Inventors: Can Hu, Irvine, CA (US); Derek D. Pham, Garden Grove, CA (US); Michael D. Lowery, Vista, CA (US)

(73) Assignee: Abbot Medical Optics Inc., Santa Ana, CA (US)

( * ) Notice: Subject to any disclaimer, the term of this patent is extended or adjusted under 35 U.S.C. 154(b) by 731 days.

(21) Appl. No.: 12/205,703

(22) Filed: Sep. 5, 2008

(65) Prior Publication Data

US 2009/0164009 A1   Jun. 25, 2009

Related U.S. Application Data

(63) Continuation-in-part of application No. 11/963,351, filed on Dec. 21, 2007.

(51) Int. Cl.
*C08G 77/38* (2006.01)
(52) U.S. Cl.
USPC .......................................... 525/474; 528/32
(58) Field of Classification Search
USPC .......................................... 528/32; 525/474
See application file for complete search history.

(56) References Cited

U.S. PATENT DOCUMENTS

| | | | |
|---|---|---|---|
| 4,647,282 A | 3/1987 | Fedorov et al. | |
| 5,217,491 A | 6/1993 | Vanderbilt | |
| 5,326,506 A | 7/1994 | Vanderbilt | |
| 5,374,663 A | 12/1994 | Daicho et al. | |
| 5,528,322 A | 6/1996 | Jinkerson | |
| 5,543,504 A | 8/1996 | Jinkerson | |
| 5,662,707 A | 9/1997 | Jinkerson | |
| 6,277,940 B1 | 8/2001 | Niwa et al. | |
| 6,310,215 B1 | 10/2001 | Iwamoto | |
| 6,326,448 B1 | 12/2001 | Ojio et al. | |
| 6,361,561 B1 | 3/2002 | Huo | |
| 6,432,137 B1 | 8/2002 | Nanushyan et al. | |
| 6,613,343 B2 | 9/2003 | Dillingham et al. | |
| 6,638,305 B2 | 10/2003 | Laguette | |
| 6,805,712 B2 | 10/2004 | Lai et al. | |
| 7,071,244 B2 | 7/2006 | Liao | |
| 2002/0071856 A1 | 6/2002 | Dillingham et al. | |
| 2004/0111151 A1 | 6/2004 | Paul et al. | |
| 2005/0070626 A1 | 3/2005 | Lowery | |
| 2005/0143751 A1 * | 6/2005 | Makker et al. | 606/107 |
| 2006/0106458 A1 | 5/2006 | Jason et al. | |
| 2008/0161913 A1 | 7/2008 | Brady et al. | |
| 2008/0161914 A1 | 7/2008 | Brady et al. | |
| 2009/0088839 A1 | 4/2009 | Hu et al. | |
| 2009/0163602 A1 | 6/2009 | Hu et al. | |

FOREIGN PATENT DOCUMENTS

| | | |
|---|---|---|
| FR | 2779940 | 12/1999 |
| WO | WO 2005/055875 | 6/2005 |
| WO | WO 2005/066662 | 7/2005 |
| WO | WO 2009/045902 | 4/2009 |
| WO | WO 2009/085996 | 7/2009 |
| WO | WO 2010/027519 | 3/2010 |

OTHER PUBLICATIONS

International Preliminary Report on Patentability and Written Opinion of PCT/US2008/087506, Jun. 22, 2010.
International Search Report of PCT/US09/030113, Mar. 23, 2009.
International Search Report of PCT/US2008/087506, Mar. 20, 2009.

* cited by examiner

*Primary Examiner* — Kuo-Liang Peng
(74) *Attorney, Agent, or Firm* — Abbott Medical Optics Inc.

(57) ABSTRACT

Described herein are silicone fluids and silicone materials that posses high glass transition temperatures ($T_g$s) when compared to conventional silicone materials. In one embodiment, an increased $T_g$ allows the formation of objects and materials by cryogenic lathing. The fluids and materials can be formed by curing silicone fluid with a cross-linker mixture comprising a cross-linker and a monofunctional hydride compound. Upon formation, the silicone materials can be extracted over long periods of time without loss of optical quality. The silicone materials can be sufficiently soft allowing folding and insertion through small incisions in the eye. Additionally, methods of forming optical silicone materials, lenses and silicone materials in general are also disclosed. In one embodiment, the method of forming a silicone based lens using cryogenic lathing techniques is described.

20 Claims, No Drawings

SOFT SILICONE MATERIALS FOR OPHTHALMIC APPLICATIONS

CROSS REFERENCE TO RELATED APPLICATIONS

This application is a continuation-in-part of application Ser. No. 11/963,351 filed Dec. 21, 2007.

FIELD OF THE INVENTION

The present invention relates to polymeric silicon materials useful in forming optical materials including, but not limited to, lenses. Methods are also described for forming and shaping lenses.

BACKGROUND OF THE INVENTION

The use of polymeric materials for medical devices is an area where vast improvements in polymeric materials have evolved and are still evolving. Physical properties of these polymers can be fine tuned for use in different environments or to behave in a predictable manner. For example, polymers for use in fabricating intraocular lenses (IOLs), need adaptation allowing for smaller incisions during implantation as well as attain a lower level of leachable content in the polymeric material itself.

Subsequently, IOLs were designed for smaller incisions through the use of elastomeric compositions that could be rolled or folded, inserted into the capsular sac and then unfolded once inside. Occasionally, folding of the IOL before insertion resulted in permanent deformation, which adversely affected the implant's optical qualities. Further, while foldable IOLs eliminated the need for the large incision, foldable IOLs were not without drawbacks. In particular, both non-deformable and foldable IOLs are susceptible to mechanical dislocation resulting in damage to the corneal endothelium.

Another approach to small incision IOL implantation uses an elastomeric polymer that becomes pliable when heated to body temperature or slightly above. Specifically, the IOL is made pliable and is deformed along at least one axis, reducing its size for subsequent insertion through a small incision. The IOL is then cooled to retain the modified shape. The cooled IOL is inserted into the capsular sac and the natural body temperature warms the IOL at which point it returns to its original shape. The primary drawback to this type of thermoplastic IOL is the limited number of polymers that meet the exacting needs of this approach. Most polymers are composed of polymethylacrylate which have solid-elastomeric transition temperatures above 100° C. Modifications to the polymer substrate require the use of plasticizers that may eventually leach into the eye causing harmful effects.

Dehydrated hydrogels have also been used with small incision techniques. Hydrogel IOLs are dehydrated before insertion and naturally rehydrated once inside the capsular sac. However, once fully rehydrated, the polymer structure is notoriously weak due to the large amount of water absorbed. The typical dehydrated hydrogel's diameter will expand from 3 mm to 6 mm resulting in an IOL that is 85% water. At this water concentration the refractive index (RI) drops to about 1.36, which is unacceptable for an IOL since lower RI materials require the optic to be thicker to achieve a given optical power.

Modern acrylate IOLs generally possess excellent mechanical properties such as foldability, tear resistance and physical strength. Acrylate IOLs also are known to possess good optical properties (transparency, high refractive index, etc.) and biocompatibility. While pure acrylic IOLs have desirable mechanical, optical and biological properties, they may have unacceptable molecular response times such that the folded or compacted IOL may not unfold as quickly as desired. A pure acrylate IOL fabricated to have a relatively fast molecular response time may be extremely tacky and lack the desired mechanical strength. In this case, the resulting IOL may tear and/or the resulting self-tack can render unfolding difficult.

Pure silicone IOLs generally possess excellent mechanical, optical and biological properties similar to pure acrylate IOLs. Unlike acrylic IOLs, silicone IOLs generally possess faster molecular response times. In fact, silicone IOLs may be so responsive that when folded small enough to be inserted through a 3 mm or smaller incision, the stored energy can cause the IOL to unfold more quickly than desired.

There is also a need for a polymeric material with a molecular response time which makes it suitable for use near fragile body tissues. There is also a need for ophthalmic devices in which one polymeric material is useful for both low modulus and high modulus applications to, inter alia, simplify the multi-part polymeric article manufacturing process and create better integrated multi-part polymeric articles in which the various parts have a common value of a property such as a refractive index.

Finally, there is a need for polymeric material that allows for a lower level of leachable material present in the lens for implantation. Presently, silicone polymeric materials used for optic soft gel implant applications suffer from an excess of leachable material resulting from a desire to keep the optic material from deforming during the manufacturing process. This presents a danger to the patient as the leachable material can begin to leach immediately upon implantation into the eye. Presently, to remedy this, multiple extraction steps are used ridding the IOL of leachables. However, each extraction causes lens material deformation and the need for remolding of the lens which comes at a great expense. Therefore, silicone materials need to be developed that allow multiple or long extraction steps without substantially deforming the lens material and which possess a substantially low leachable content when implanted into the eye.

SUMMARY OF THE INVENTION

Described herein are silicone materials that posses relatively high glass transition temperatures ($T_g$s) when compared to conventional silicone materials. The silicone materials are formed from silicone fluids. In one embodiment, an increased $T_g$ allows the formation of objects and materials by cryogenic lathing. The silicone materials, elastomers or gels can be formed by curing silicone fluid with a cross-linker mixture. The cross-linker mixture can comprise at least one cross-linker and at least one monofunctional hydride compound and when reacted with the silicone fluids described herein can form a silicone material that is soft and possesses a high glass transition temperature compared to existing silicone fluids. Upon formation, the silicone materials can be extracted over long periods of time without loss of optical quality. In one embodiment, upon formation, the silicon materials can have a sufficiently low amount of leachable content or can retain optical quality even after long extraction steps. Further, the silicone materials can be sufficiently soft allowing folding and insertion through small incisions in the eye. Additionally, methods of forming optical silicone materials and lenses, in general, are also disclosed. In one embodiment, the method of forming a lens comprising a silicone material using cryogenic lathing techniques is described.

In one embodiment a silicone material is described comprising a silicone fluid with a general structure of formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$; wherein at least one of $R^1$, $R^2$, $R^3$, $R^6$, $R^7$, $R^8$ is $CH=CH_2$; and wherein the lens has a $T_g$ greater than −70° C. and contains a total leachable content of less than about 20%.

In one embodiment, the lens has a compression modulus less than about 200 kPa. In another embodiment, the lens has

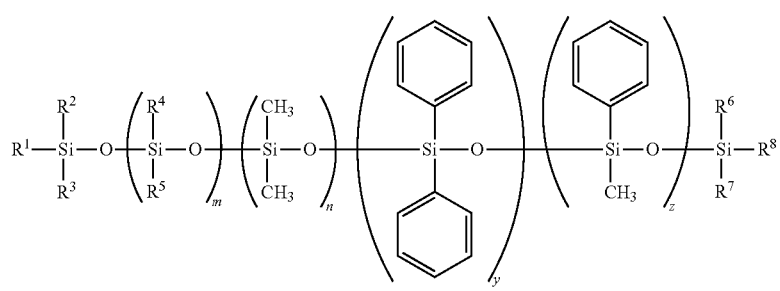

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$; wherein at least one of $R^1$, $R^2$, $R^3$, $R^6$, $R^7$, $R^8$ is $CH=CH_2$; and wherein the silicone material has a $T_g$ greater than −70° C. and contains a total leachable content of less than about 20%.

In one embodiment, the silicone material has a compression modulus less than about 200 kPa. In another embodiment, the silicone material has a compression modulus less than about 100 kPa.

In one embodiment, the silicone material can be formed into a lens. In another embodiment, the lens has refractive index of less than about 1.55. In yet another embodiment, the lens is an intraocular lens.

In one embodiment, the silicone material is capable of controlled release of an active agent.

Also described herein, in one embodiment, is a lens comprising a silicone fluid with a general structure of formula 1 a compression modulus less than about 100 kPa. In one embodiment, the lens has a refractive index of less than about 1.55. In another embodiment, the lens is an ocular lens selected from the group consisting of in intraocular lens and a contact lens. In yet another embodiment, the intraocular lens comprises an optic component and at least one haptic.

In one embodiment, the lens comprises a cross-linker mixture. In another embodiment, the cross-linker mixture comprises a cross-linker and a monofunctional hydride compound.

In one embodiment, the lens is capable of controlled release of an active agent.

Further described herein is a method of forming at least a portion of a lens comprising the steps of: (a) providing silicone fluid of a general structure of formula 1

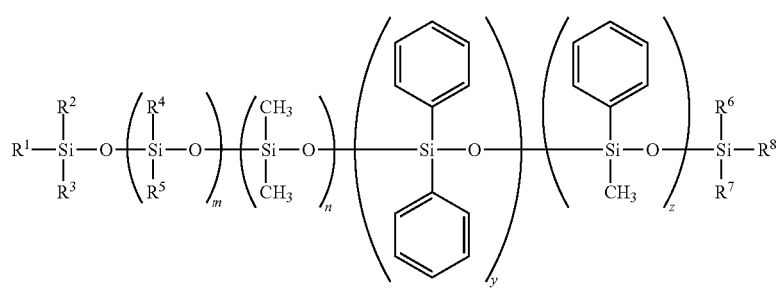

Formula 1

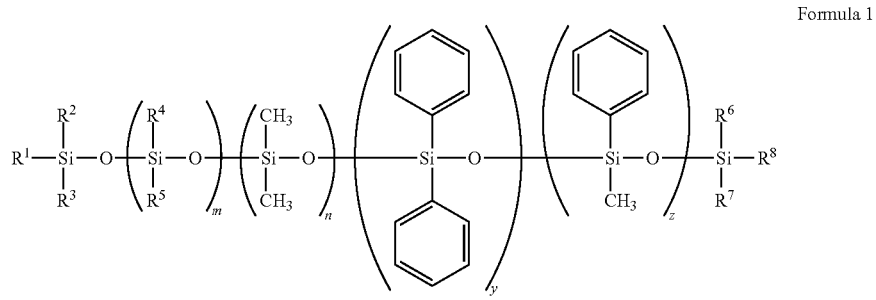

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$; and wherein at least one of $R^1$, $R^2$, $R^3$, $R^6$, $R^7$, or $R^8$ is $CH=CH_2$; b) providing a cross-linker mixture; c) providing a catalyst; d) combining the silicone fluid, the cross-linker mixture and the catalyst thereby forming a polymer mixture; (e) setting up a mold with said polymer mixture thereby forming a molded optic material; (f) curing said molded optical material thereby forming a cured optic material, wherein said cured optic material has a $T_g$ greater than $-70°$ C.; and (g) cryolathing said cured optic material to form a lens. In one embodiment, the optic material is extracted prior to step (e), thereby attaining a polymer with a total leachable content of less than about 20%.

In one embodiment, the lens has a compression modulus less than about 200 kPa. In another embodiment, the lens has a compression modulus less than about 100 kPa. In yet anther embodiment, the lens has a refractive index of less than about 1.55.

In one embodiment, the lens is an ocular lens selected from the group consisting of in intraocular lens and a contact lens. In another embodiment, intraocular lens comprises an optic component and at least one haptic.

In one embodiment, the cross-linker mixture comprises a monofunctional hydride compound.

Further still, described herein is a method of forming an optic lens comprising the steps of: a) providing silicone fluid having a general structure of formula 1 b) providing a cross-linker mixture; c) providing a catalyst; d) combining the silicone fluid, the cross-linker mixture and the catalyst thereby forming a silicone mixture; e) curing said silicone mixture to form an optic lens; and f) extracting said optic lens to attain an extracted optic lens having a total leachable content of less than about 20% and a $T_g$ greater than about $-70°$ C. In one embodiment, the cross-linker mixture contains a cross-linker and a monofunctional hydride compound.

DEFINITION OF TERMS

The terms and phrases used herein shall have the following, non-limiting, definitions.

Clear Aperture: As used herein, "clear aperture" refers to the portion of an optic that limits the extent of the rays from an object that contributes to the conjugate image and is generally expressed as a diameter of a circle.

Common Polymeric Material: As used herein, "common polymeric material" refers to similarity of material composition between two objects or portions of an object. Two objects or portions of an object comprise a common polymeric material if the two objects or portions consist essentially of the same base polymer chain or have at least 50% w/w of the same base polymer chain, or 75% w/w of the same base polymer chain, or 85% w/w of the same base polymer chain, or 90% w/w of the same base polymer chain, or 95% w/w of the same base polymer chain, and, when present, the same cross-linking agent.

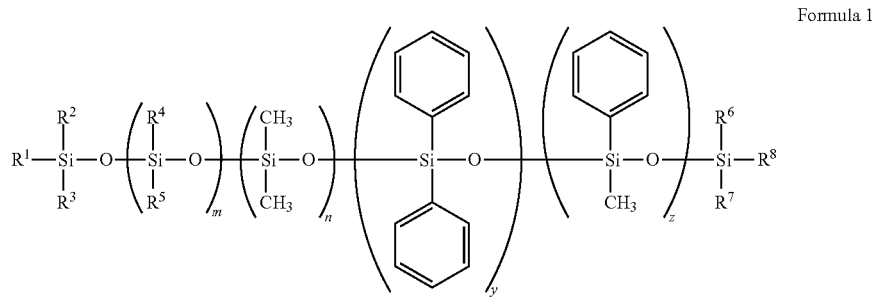

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$; wherein at least one of $R^1$, $R^2$, $R^3$, $R^6$, $R^7$, or $R^8$ is $CH=CH_2$;

Common Refractive Index: As used herein, "common refractive index" refers to the similarity of refractive indices between two materials. A common refractive index between two materials is a difference in refractive index between the two materials of less than or equal to 5%, or less than or equal to 2%, or less than or equal to 1%, or less than or equal to 0.5%.

Compression Modulus or Modulus of Elasticity: As used herein "modulus of elasticity" refers to the ratio of stress to strain. As used herein, "compression modulus" refers to the ratio of compressive stress to compressive strain.

Elongation: As used herein, "elongation" refers to the act of lengthening or stretching a polymeric material.

Full Elongation: As used herein, "full elongation" refers to the act of lengthening or stretching a polymeric material or polymeric IOL to its elastic limit.

Glass Transition Temperature ($T_g$): As used herein, the "glass transition temperature" or "($T_g$)" refers to the temperature wherein a polymeric material becomes less elastic and more brittle.

Intermediate Elongation: As used herein, "intermediate elongation" refers to the act of lengthening or stretching a polymeric material or polymeric IOL to a point between its original length and limit.

kPa: As used herein, "kPa" refers to kilopascal, which is a unit of pressure or stress and is the equal to 1000× Newton per meter squared ($N/m^2$).

Leachable Content: As used herein, "leachable content" or "leachables" refers to substances remaining in a formed or cured polymeric material which is unreacted or unbound to the polymer. Such material can include, but is not limited to, unreacted monomer, unreacted oligomer, unreacted macromer, catalysts, methylvinyl cyclic compounds, solvents, monofunctional hydride compounds or cross-linkers, dyes, stabilizers, and the like.

Mass percent: As used herein, "mass percent" and "mass %" refer to the mass of monomer present in a polymer divided by the total weight of the polymer multiplied by 100. Mathematically, mass percent is represented by the following formula where $M_m$ is the mass of the monomer and $M_P$ is the mass of the corresponding polymer: $[M_m/M_P] \times 100 =$ Mass Percent.

Moduli: As used herein, "moduli" refers to the plural form of modulus or modulus of elasticity.

Percent Elongation: As used herein, "percent elongation" refers to the length of an elongated polymer divided by the length of the original polymer. Mathematically, the percent elongation is represented by the following formula where L is the length of the elongated polymer and $L_0$ is the length of the corresponding non-elongated polymer: $[L/L_0] \times 100 =$ Percent Elongation.

Pliable: As used herein, "pliable" refers to the flexible nature of a polymeric material and to the flexibility of polymeric IOLs that can be folded, rolled or otherwise deformed sufficiently to be inserted through a 2 mm or less surgical incision.

Refractive Index (RI): As used herein, "refractive index" or "(RI)" refers to a measurement of the refraction of light of a material or object, such as an IOL. More specifically, it is a measurement of the ratio of the speed of light in a vacuum or reference medium to the speed of light in the medium under examination. The refractive index of a material or object typically varies with the wavelength of the light, a phenomenon sometimes referred to as dispersion.

Resiliency: As used herein, "resiliency" refers to a polymeric material's, or a polymeric IOL's, inherent ability to return to its unstressed configuration following impact, deformation in an inserter, or the resulting deformation associated with the stress on impact, also referred to herein after as "rebound resiliency."

Softness: As used herein, "softness" refers to a polymeric material's, or a polymeric IOL's, pliability as opposed to, for example, a polymethylmethacrylate (PMMA) IOL that is rigid and hard.

Ultimate Tensile Strength: As used herein, "ultimate tensile strength" refers to the maximum stress a material can withstand before fracture and is measured in psi ($lb/in^2$).

DETAILED DESCRIPTION OF THE INVENTION

Described herein are silicone materials that posses high glass transition temperatures ($T_g$s) when compared to conventional silicone materials. The silicone materials are formed from silicone fluids. In one embodiment, an increased $T_g$ allows the formation of silicone materials, formed from silicone fluids, by cryogenic lathing. The silicone materials can be formed by curing silicone fluid with a cross-linker mixture. In one embodiment, the cross-linker mixture is a true cross-linker and a monfunctional hydride compound, which forms a material that is soft enough and possesses a low enough leachable content that, upon formation, can be extracted for over long periods of time without loss of optical quality. The silicone materials can be sufficiently soft allowing folding and insertion through small incisions in the eye. Additionally, methods of forming optical silicone materials and lenses, in general, are also disclosed. In one embodiment, the method of forming a lens comprising a silicone material using cryogenic lathing techniques is described.

As for intraocular lenses (IOLs), it is desirable they can be folded, rolled or otherwise deformed such that they can be inserted into the eye through small incisions. Furthermore, in order to reduce patient trauma and post surgical recovery time, the IOL preferably comprises a responsive polymer that unfolds in a controlled manner. To meet these requirements, the polymers preferably have minimal self tack and do not retain excessive amounts of stored mechanical energy. However, if the IOL is too thin, or the polymer lacks sufficient mechanical strength, it may be too fragile and easily dislocated or damaged during or after the insertion process.

Historically, foldable IOL materials have been designed to be tough (tensile strength of greater than 750 pounds per square inch [psi]) with a relatively high percent elongation (greater than 100%). These properties give the IOL sufficient toughness such that the IOL does not tear from the forces experienced during insertion through a 2.6 to 3.2 mm incision. Presently available foldable IOLs include, among others, Sensar® (Advanced Medical Optics, Santa Ana, Calif.), an acrylic IOL having a tensile strength of about 850 psi and an elongation at break of about 140%; CLARIFLEXE (Advanced Medical Optics), a silicone IOL having a tensile strength of about 800 psi and an elongation at break of about 230%; and AcrySof® (Alcon Laboratories, Fort Worth, Tex.) having a tensile strength of about 1050 psi. All three IOLs are suitable for insertion through incision sizes of about 2.6 mm or greater. The silicone materials described herein are soft to very soft and may be foldable.

Flexibility in monomer selection is provided herein, which provides for control over the material's mechanical, optical and/or thermal properties. For example, the ability to adjust a material's refractive index (RI) and mechanical properties is important in designing ultra-small incision IOLs. Also, hydrophobic siloxy materials have demonstrated excellent ocular biocompatibility. Thus, it surprisingly has been discovered that by utilizing the silicone materials in the preparation of IOL materials, an IOL optic can be made that has properties permitting its passage through an ultra small incision without damage to the IOL, the inserter cartridge, or the eye. In addition, the IOL can have at least one resilient haptic that shares a common siloxy monomer with the optic.

Silicones have unique properties derived from the inherent flexibility of the siloxane bond. The alternating silicon-oxygen polymer backbone of siloxanes makes them remarkably more flexible than their organic counterparts that have a carbon-oxygen backbone. This property of siloxanes generally, results in lower glass-transition temperatures ($T_g$) and excellent flexibility. Furthermore, a low initial modulus is another important attribute of siloxanes. In order to pass through the insertion cartridge, a conventional refractive IOL must be capable of elongating up to about 100%. Therefore, it is important that the initial modulus be at optimum levels. A low initial modulus translates to low stimulus required to express the IOL through the cartridge. Further, when the appropriate amounts of selected siloxanes, cross-linkers or cross-linker mixture and catalysts are combined, the resulting material has the flexibility and modulus required to make, for example, the optic portion of an IOL suitable for insertion through a small incision without harming the IOL, the inserter cartridge or the eye.

In some embodiments, an intraocular lens comprises an optic and a haptic made from a common polymeric material such that they have a common refractive index; however, the optic and haptic have mechanical properties that are different for each. In some embodiments, the IOL is formed according to an embodiment so that the optic and haptic have different moduli of elasticity. For example, an accommodating IOL is formed so that the optic has a lower modulus than the haptic, thus allowing the relatively stiff haptic to protrude inside the relatively soft optic without causing unwanted reflections due to a refractive index mismatch at interfaces between the optic and the protruding haptic. Examples of accommodating IOLs having a stiffer protruding haptic are disclosed in co-pending U.S. patent application Ser. Nos. 11/618,411 and 11/618,325, which are herein incorporated by reference in their entirety. One way to adjust moduli between the haptic and optic is provided by an adjustment in the amount of cross-linker and/or catalyst and/or methylvinylcyclic (MVC) content of each IOL component. Embodiments herein are used to provide IOL's in which at least the optic thereof has a modulus that is less than about 500 kPa, less than about 200, less than about 100 kPa, less than 70 kPa, or even less than 50 kPa or 25 kPa. The stiffness of the haptic may be greater than 500 kPa, or greater than 3000 kPa, depending on the particular design requirements. In some embodiments, the modulus of the haptic is greater than that of the optic by at least 50%, by at least 150%, by at least 250%, or by at least 500%. In some embodiments, the modulus may vary continuously over at least some interface regions between the haptic and the optic, for example, to provide a particular performance or stress distribution over the IOL in reaction to an external force on the IOL (e.g., an ocular force produced by the capsular bag, zonules, or ciliary muscle of an eye into which the IOL is inserted).

In some embodiments, an ophthalmic lens, such as an intraocular lens, comprises an optic having a clear aperture that comprises an inner portion and an outer portion disposed about said inner portion. The inner portion and outer portion comprise a common polymeric material and may have a common refraction index; however, the inner portion has a modulus that is different from that of the outer portion. The difference in modulus may be selected, for example, to control the amount and/or form of deformation of the optic in reaction to an external force such as an ocular force produced by the capsular bag, the zonules, and/or the ciliary muscle of an eye into which the optic is placed. In some embodiments, the refractive index also varies between the zones, for example, to control aberrations of the optic in a stressed or unstressed state.

The modulus of the inner portion of the optic may by greater than or less than that of the outer portion, depending of the particular design requirements. In some embodiments, the optic comprises three or more zones disposed within the clear aperture of the optic. In other embodiments, the modulus of at least portions of the optic varies continually, for example, by producing a catalyst gradient throughout a polymeric fluid used to form the optic. In some embodiments, the zones of the optic have an ellipsoid or similar shape, such that the modulus varies from the center of the optic outward in a three-dimensional manner. Alternatively or additionally, the variation in modulus of the zones varies in a two dimensional manner, for example, forming concentric rings as the modulus varies in radial direction from the optical axis of the optic. The difference in modulus between two zones of the optic may be greater than or equal to 5%, or greater than or equal to 15%, or greater than or equal to 25%, or greater than or equal to 50%, depending on the number of zones and the desired performance of the optic under a given loading force.

Some embodiments provide a silicone material that is particularly suitable for use in at least the optic of an accommodating IOL. For example, an adjustment in the amount of cross-linker or type of cross-linker, the use of a cross-linker mixture, the use of a monofunctional hydride compound, number of vinyl terminations, number of vinyl pendent groups, catalyst and/or MVC content, the haptic portion of an IOL or accommodating IOL are made. Certain embodiments provide IOL's in which at least the optic thereof has a modulus that is less than about 500 kPa, less than about 200, less than about 100 kPa, less than 70 kPa, or even less than 50 kPa or 25 kPa. The stiffness of the optic may be greater than 500 kPa, or greater than 3000 kPa, depending on the particular design requirements. The modulus, in some embodiments can be between about 100 kPa and about 50 kPa, or between 200 about kPa and about 100 kPa, or 200 kPa and 50 kPa.

The silicone materials made may have low initial moduli and a low $T_g$. In other embodiments, the $T_g$ may be higher to allow for different types of manufacturing methods. In one embodiment, the $T_g$ of the silicone material is preferably above $-100°$ C., above $-80°$ C., above $-75°$ C., above $-60°$ C., above $-50°$ C., above $-35°$ C. or above $0°$ C. Moreover, the IOLs may be multifocal (i.e. refractive or diffractive), accommodating (i.e. deformable or movable under the normal muscle movements of the human eye), highly biocompatible and have R is ranging from about 1.40 to about 1.56, preferably from about 1.41 to about 1.53, for light in the visible wavelengths. These and other objects described herein are achieved by providing an unsaturated terminated silicone fluid (herein referred to as "silicone fluid") and cross-linking it using a hydride cross-linker mixture and platinum catalyst. In one embodiment, a monofunctional hydride compound is used. The silicone fluid, in some embodiments, has more than three vinyl terminations. In different embodiments, the silicone fluid has three, four, five or six vinyl terminations. In other embodiments, metals aside from platinum, more preferably transition metals, may be used. Herein, silicone fluids, in some embodiments, are cross-linked thereby providing polymers with different moduli.

The silicone fluids are preferably vinyl terminated siloxanes, more preferably multi-vinyl terminated. Non-limiting examples include vinyl terminated diphenylsiloxane-dimethylsiloxane copolymers, vinyl terminated polyphenylmethylsiloxanes, vinyl terminated phenylmethylsiloxane-diphenyldimethylsiloxane copolymers, vinyl terminated polydimethylsiloxanes and methacrylate, and acrylate functional siloxanes. Other suitable silicone materials are disclosed in U.S. Pat. No. 6,361,561, the entirety of which is incorporated herein by reference. Representative materials can be obtained from Gelest, Inc. (Morrisville, Pa.) or synthesized using methods known to those skilled in the art.

In one embodiment, the silicon fluid is a vinyl terminated siloxane comprising polymers of the structure depicted in Formula 1 below. In other embodiments, polymers can consist of greater than 50% w/w of Formula 1, or greater than 75% w/w of Formula 1, or greater than 85% w/w of Formula 1, or greater than 90% w/w of Formula 1, or greater than 95% w/w of Formula 1.

In another embodiment, at least four of $R^1$, $R^2$, $R^3$, $R^6$, $R^7$, and $R^8$ are $CH=CH_2$. In another embodiment, at least five are $CH=CH_2$. In yet another embodiment, all six of $R^1$, $R^2$, $R^3$, $R^6$, $R^7$, and $R^8$ are $CH=CH_2$. The utility of more vinyl terminations, as well as vinyl pendent groups, is to provide the polymer with additional ability to crosslink, the ability to bind molecules it would otherwise not be able to bind and provide additional sites of chelation.

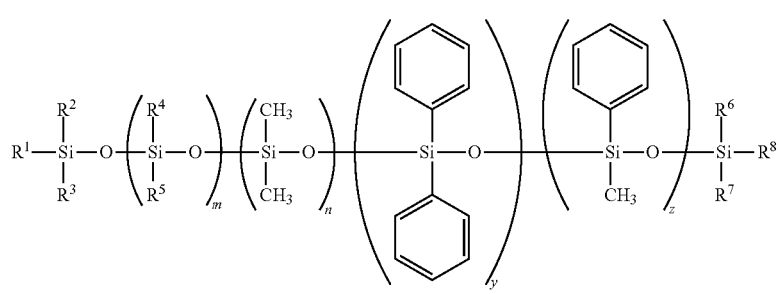

Formula 1

The values for x, y, and z will vary depending on, for example, the desired RI of the lens. In Formula 1, x is equal to the sum of m and n and is preferably at least about 1. In one embodiment, the sum of x, y, and z is greater than or equal to about 1. In another embodiment, x ranges from about 0 to about 12000, or from 0 to about 6000, or from 0 to about 1000 or from 0 to about 500, or from 0 to about 250, or from 0 to about 125, or from 0 to about 50. In another embodiment, y ranges from 0 to about 500, or from 0 to about 250, or from 0 to about 125, or from 0 to about 50. In another embodiment, z ranges from 0 to about 500, or from 0 to about 250, or from 0 to about 125, or from 0 to about 50.

Preferably, IOLs produced have an RI of at least 1.40, more preferably at least 1.43. For example, if an IOL having a RI of 1.43 is desired, the x:y:z ratio may be approximately 30:1:1; a x:y:z ratio of about 12:1:2 will result in an IOL having a RI of approximately 1.46. Skilled artisans can prepare an IOL having a desired RI, optical clarity and mechanical properties by adjusting the x:y:z ratio using skills known in the art and without undue experimentation.

In one embodiment, x ranges from about 0 to about 12000, y ranges from about 0 to about 500, z ranges from 0 to about 500, and the sum of x, y, and z is greater than or equal to 1. In another embodiment, x ranges from about 10 to about 12000, y ranges from 1 to about 500, z ranges from 0 to about 500, and the sum of x, y, and z is from about 100 to about 15000. In another embodiment, the sum of x, y and z has a minimum value of about 200 in order to provide a high softness polymer (e.g., when required for optic portions of an IOL). $R^1$-$R^8$ are each independently $CH_3$, $C_6H_5$ or $CH=CH_2$. If m is greater than zero, at least one of $R^4$ or $R^5$ must be $CH=CH_2$. In one embodiment, more than two of $R^1$, $R^2$, $R^3$, $R^6$, $R^7$, and $R^8$ are $CH=CH_2$.

In one embodiment, the silicone fluid can be hexavinyl terminated, wherein $R^1$, $R^2$, $R^3$, $R^6$, $R^7$, and $R^8$ are vinyl terminated and is represented by Formula 2. In other embodiments, polymers can consist of greater than 50% w/w of Formula 2, or greater than 75% w/w of Formula 2, or greater than 85% w/w of Formula 2, or greater than 90% w/w of Formula 2, or greater than 95% w/w of Formula 2. The values for x, y, and z will vary depending on, for example, the desired RI of the lens. In one embodiment, the sum of x, y, and z is greater than or equal to about 1. Preferably, IOLs produced have an RI of at least 1.40, more preferably at least 1.43. For example, if an IOL having a RI of 1.43 is desired, the x:y:z ratio may be approximately 30:1:1; a x:y:z ratio of about 12:1:2 will result in an IOL having a RI of approximately 1.46. Skilled artisans can prepare an IOL having a desired RI, optical clarity and mechanical properties by adjusting the x:y:z ratio using skills known in the art and without undue experimentation. In one embodiment, x ranges from about 0 to about 12000, y ranges from about 0 to about 500, z ranges from 0 to about 500, and the sum of x, y, and z is greater than or equal to 1. In another embodiment, x ranges from about 10 to about 1200, y ranges from about 1 to about 500, z ranges from 0 to about 500, and the sum of x, y, and z is from about 100 to about 2200. In another embodiment, the sum of x, y and z has a minimum value of about 200 in order to provide a high softness polymer (e.g., when required for optic portions of an IOL). If m is greater than zero, at least one of $R^4$ or $R^5$ must be $CH=CH_2$.

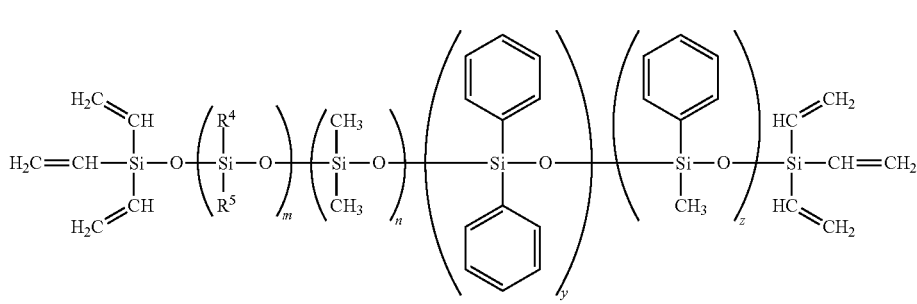

Formula 2

Combinations for the sum of x, y and z exist for sums from at least 1 to about 15000. In addition, the sum can determine what type of material is formed. In one embodiment, for example, the sum can be less than about 100, in which case, the material can be a liquid and can be used as a liquid carrier formulation, for example, eye drops or hair spray. In another embodiment, the sum can be from about 100 to about 1000, wherein the material can be a more viscous liquid or gel. In one embodiment, the material can be used in topical compositions, for example, skin creams and lotions. In one embodiment, the skin cream absorbs harmful light. In another embodiment, the sum can be from about 300 to about 1200, wherein the material can be formed as an elastomeric. In such an embodiment, the materials formed as elastomerics can be used to form such items as lenses. Each of the embodiments described above can be used with other appropriate additives with or without further cross-linking reactions.

Optionally, a number of ultraviolet (UV) and blue light absorbing dyes can be added to the silicone materials described herein. For example, silicone IOLs, formed from at least in part the silicone material described herein, may include 0.1 to 1.5 mass % of UV and blue light absorbing compounds such as benzophenone and benzotriazole-based UV light absorbers or blue light blocking dyes including azo and methine yellow, which selectively absorb UV/blue light radiation up to about 450λ. See, for example, U.S. Pat. Nos. 5,374,663; 5,528,322; 5,543,504; 5,662,707; 6,277,940; 6,310,215 and 6,326,448, the entire contents of which are incorporated herein by reference.

A variety of initiators for polymerization reactions can be employed. In one non-limiting embodiment, peroxide initiators are used. Examples of peroxide initiators include, without limitation, about 0.1 to about 1.5 mass % of di-tert-butyl peroxide (Trigonox® a registered trademark of Akzo Chemie Nederland B.V. Corporation Amersfoort, Netherlands) or 2,5-dimethyl-2,5-bis (2-ethylhexanoylperoxy) hexane. It should be noted that peroxide initiators initiate the cross-linking of vinyl groups on monomers (e.g., those on divinyl-terminated silicone monomers). While this can help facilitate the cross-linking of the silicone fluids, at least some of the hydride groups must still be cross-linked.

One or more silicone fluid may be cross-linked utilizing one or more hydride-containing cross-linker such as, but not limited to, nonpolymetric X-linkers such as phenyltris(dimethylsiloxy)silane (Formula 3 below), tetrakis(dimethylsiloxy)silane (Formula 4 below), 1,1,3,3-tetraisopropyldisiloxane, 1,1,3,3-tetramethyldisiloxane, 1,1,4,4-tetramethyldisilethane bis(dimethylsilyl)ethane, 1,1,3,3-tetramethyldisilazane; hydride terminated polymeric X-linkers with different molecular weights such as DMS-H03, DMS-H11 to DMS-H41, hydride terminated polyphenyl-(di-methylhydrosiloxy)siloxane (HDP-111, Formula 5 below, wherein W is about 5 to about 50); HPM-502, which are commercially available from Gelest; nonhydride terminated polymeric cross-linkers such as XL-103, XL-110, XL-111, XL-112, XL-115, which are commercially available from Nusil; and HMS-013, HMS-031, HMS-082, HMS-301, HMS-991, which are commercially available from Gelest. Other cross-linkers such as hydride Q resins can also be used thereby improving the mechanical properties of the silicone materials (the silicone material commonly form gels). The softness of the final silicone material formulations depends on the relative amount of cross-linker to vinyl silicone fluid (i.e. HN [hydride-vinyl] ratio).

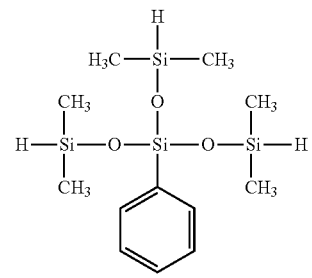

Phenyltris(dimethylsiloxy)silane

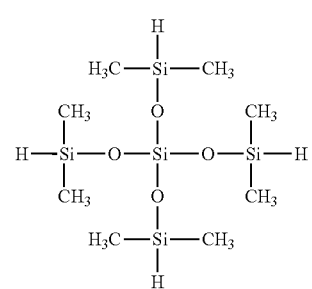

Tetrakis(dimethylsiloxy)silane

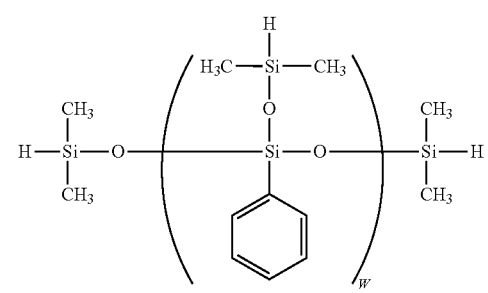

Hydride-terminated Polyphenyl-(di-methylhydrosiloxy)siloxane

Monofunctional hydride compounds, such as but not limited to, monohydride terminated siloxanes can also be used herein. The inventors surprisingly found that using one or more monofunctional hydride compound allows for the formation of a softer lens material with unexpected properties that will be discussed further herein. Compounds such as, but not limited to monohydride terminated polydimethylsiloxanes are useful in creating lens materials with the appropriate softness. Some exemplary, non-limiting monohydride compounds are MCR-H07 and MCR-H21 from Gelest. In one embodiment, a monfunctional hydride compound can be one of formula 6

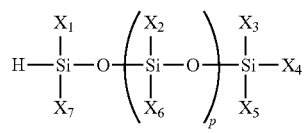

wherein $X_1$-$X_7$ are each independently selected from a $C_1$-$C_{10}$ aliphatic or aromatic group and p is from about 1 to about 1000.

In one embodiment, the silicone materials described herein are soft due to the use of a monofunctional hydride compound. Not to be bound by theory, but it is believed that the unique behavior of select silicone fluids described herein is attributed to the use of a monofunctional hydride compound. Using a monofunctional hydride compound allows for less intertwining of polymer material as there is only one active site on the hydride compound which caps the functional site of the silicone fluids.

In one embodiment, a cross-linker mixture is used. A cross-linker mixture comprises an appropriate amount of a cross-linker and an appropriate amount of a monofunctional hydride compound, both mentioned above. Using such a mixture allows the artisan to fine tune the softness of the lens by "capping" a certain amount of the functional hydride groups on the polymer using monofunctional hydride compounds, while allowing a particular amount of the hydride functional groups on the polymers to cross-link.

Properties of the silicone materials such as modulus, percent weight loss can be changed by varying the ratio of hydride and vinyl contents (HN ratio) in the silicone fluids. Vinyl content of a silicone fluid may be estimated or determined by, for example, the GPC method, titration, or NMR (nuclear magnetic resonance spectroscopy). By varying the ratio of hydride primarily from the cross-linker and vinyl primarily from the vinyl silicone fluid, silicone materials with different moduli are obtained. In certain embodiments, the HN ratio is at least about 0.1, more preferably at least about 0.5, more preferably about 0.6, more preferably about 0.7, more preferably about 0.8, more preferably about 0.9, more preferably about 1.0, more preferably about 1.1, more preferably about 1.25, and more preferably at most about 1.5.

In certain embodiments, the modulus of material can be affected by the amount of catalyst and/or MVCs. In certain embodiments, as the amount of catalyst and/or MVCs is increased, the modulus of the material also increases until a peak modulus is reached. In certain embodiments, after a peak modulus is reached, the modulus begins to level off or, in some cases, decreases.

In certain embodiments, the MVC can be any methylvinyl siloxane, which includes cyclosiloxane and non-cyclosiloxane classes of materials. Nonlimiting examples of methylvinyl cyclosiloxane classes include tetramethylvinylcyclotetrasiloxane and pentamethylvinylcyclopentasiloxane. Non-cyclosiloxane classes include, but are not limited to, 1,3-tetramethyldisiloxane, divinyltetraphenyldisiloxane, 1,5-divinylhexamethyltrisiloxane, and 1,5-divinyl-3,3-diphenyltetramethyltrisiloxane. One example of an MVC is 1,3,5,7-tetravinyl-1,3,5,7-tetramethylcyclotetrasiloxane. In certain embodiments, the MVC is present in an amount of at least about 0.01% or at most about 1% by weight. It should be understood that for certain polymer embodiments described herein, MVCs can partially substitute the catalyst, augment the catalyst or be used to alter the HN ratio. The MVC, in certain embodiments, has an inversely proportional impact on the moduli of polymers prepared therewith.

Exemplary platinum catalysts include, but are not limited to, platinum-tetravinyltetramethylcyclotetrasiloxane complex, platinum carbonyl cyclovinylmethylsiloxane complex, platinum cyclovinylmethylsiloxane complex, and platinum octanaldehyde/octanol complex. Many different platinum catalysts can be used depending on, inter alia, the desired pot life. Preferably, the platinum catalyst is used in amounts by weight of at least about 0.01%, more preferably at least about 0.05%, even more preferably at least about 0.1%. Preferably, the platinum catalyst is used in amounts of about 1% or less, more preferably about 0.75% or less, even more preferably about 0.5% or less, even more preferably about 0.4%, even more preferably about 0.3%, even more preferably about 0.2%.

In addition to platinum catalysts, other metal catalysts can be used. In some embodiments, transition metals are used as catalysts, more specifically, palladium and rhodium catalysts can be used. Complexes and salts of metal catalysts can also be suitable. An example of a transition metal complex used as a catalyst is tris(dibutylsulfide) rhodium trichloride.

For certain embodiments, and without wishing to be bound by theory, one reason for the impact of some catalysts, especially platinum catalysts, on the modulus can be due to the presence of an inhibitor or stabilizer that reduces the hydride/vinyl ratio and/or prevents complete curing. An example of such an agent is an MVC such as cyclovinylmethylsiloxane (e.g., 1,3,5,7-tetravinyl-1,3,5,7-tetramethylcyclotetrasiloxane). It is worthwhile to note that in certain embodiments, the effects of catalyst amounts on modulus is independent of curing time. While MVCs are sometimes used as stabilizers in catalysts to, for example, keep platinum suspended in solution, the MVCs can be present in such small amounts that they may be inert.

In certain embodiments, the platinum catalyst level for a polymer is increased to levels significantly higher than conventionally used (e.g., up to 50 ppm versus a more traditional 10 ppm or less). A skilled artisan expects that as catalyst concentration increases, curing time can decrease and silicone fluid cross-linking can increase. The skilled artisan also expects this to lead to a more rigid or firm polymer (even assuming curing temperature may be the same). In certain embodiments, the catalyst is increased to atypical levels and a significant decrease in curing time can be observed.

In certain embodiments, the resulting silicone material is far less rigid and less firm than expected. In certain embodiments, excessive amounts of catalyst are used and the corresponding increase in MVCs allows them to become reactive ingredients and end-cap the hydrides on the cross-linkers, which results in more free ends on the structural silicone materials. The additional free ends can provide a less cross-linked and, therefore, less rigid silicone material.

In certain embodiments, the MVC is present in an amount of at least about 0.01%, about 0.05%, about 0.1%, about 0.11%, about 0.15%, about 0.2%, or about 0.25% by weight; to at most about 1%, about 0.75%, about 0.5%, about 0.4%, about 0.39%, about 0.35%, or about 0.35% by weight. In certain embodiments, the MVCs partially substitute the catalyst in any proportion or amount including completely or the MVC may augment the catalyst. In certain embodiments, the MVC has an inversely proportional impact on the moduli of silicone materials prepared therewith. Certain embodiments described herein may incorporate the teachings regarding MVCs and their relationship to the moduli of silicone materials prepared therefrom.

When used for IOL optic portions, a silicone material with a low initial modulus prepared as described herein facilitates a more easily inserted IOL by reducing the force required to express the silicone based IOL through an inserter cartridge. In addition, the same starting materials can be used for both optic and haptic portions (only varying the HN ratio and/or % catalyst or, MVC); therefore, the material supply and manufacture of IOLs is simplified. An added benefit of using the same starting materials is that the resulting optic and haptic portions will be more compatible thereby facilitating more robust and/or seamless fusion.

In one embodiment, the silicone material is used as a controlled release polymer for formulating therapeutic agents. In addition, the silicone material can be used to prepare dual use implantable or wearable medical devices (e.g., IOLs and contact lenses) whereby the device serves a particular purpose as well as controllably releasing therapeutic agents. For example, the silicone material can be used to prepare an IOL that controllably releases a therapeutic agent for "dry eye." A skilled artisan can envision several devices, conditions, and/or therapeutic agents in conjunction with this embodiment.

The lenses formed of silicone materials described herein are advantageous as they can retain optical quality even through hours of solvent extraction. Solvent extraction is a necessary step in lens production as leachable material is removed from the lens material during this process. If leachables are not removed prior to implantation into a patient, long term leaching and lens shrinkage can be a problem. Additionally, long term shrinkage can lead to a diminished optical quality of the lens. A typical silicone based optical material will generally loose optical quality, shrink and/or deform in shape when subjected to one or more solvent extractions. In fact, it is not uncommon to require one or more remolding steps after each extraction of the silicone material.

The silicone materials described herein, in some embodiments, do not lose optical quality when subjected to solvent extraction for more than one hour, more than three hours, more than five hours or more than a day. In one embodiment, the extraction can be a soxhlet extraction.

Further still, the silicone materials with monofunctional hydride compounds can have a lower amount of leachable material once cured. Not to be bound by theory, but it is believed that the use of monofunctional hydride compounds leads to less unreacted silicone fluid intertwined within the cured silicone material. Therefore, in one embodiment, the percentage of leachable material is less that about 20% or less than about 17%, or less than about 15%. In one embodiment, for example, the silicone material can have less than 20% leachable content and after one or more extraction steps can have a leachable content less than about 15%.

Further, the silicone materials with high refractive index can have a higher $T_g$ which can aid in manufacturing processes as described below. The silicone materials comprising a monofunctional hydride compound can have a $T_g$ greater than −100° C., or greater than −70° C., or around −50° C.

This increased $T_g$ can have many impacts on the silicone materials physical characteristics. In one embodiment, one important characteristic is that a silicone material with a high $T_g$, such as one higher than −70° C., can be lathed under cryogenic temperatures. The process of cryolathing entails placing the silicone material, for example a lens, into a lathing chamber. The silicone material is then slowly cooled to a specific cryogenic temperature. Once the silicone material has reached the specific cryogenic temperature, it is lathed and formed into the appropriate shape. After the silicone material has been lathed, it is allowed to warm again to room temperature within the chamber. Not to be bound by theory, but it is believed that cooling the silicone material can induce an atomic level alignment of the atoms in the silicone material making it more resilient. Therefore, this method can be highly advantageous.

Previous silicone materials, with $T_g$s less than, for example, −70° C., would deteriorate under cryogenic conditions, making them inappropriate for cryogenic lathing procedures. Such materials may loose optical properties after extraction of leachable content. Materials with $T_g$s above, for example −70° C. for example can be suitable for cryogenic lathing processing and manufacture. Such materials can in some embodiments undergo extraction of leachable content and then be lathed under cryogenic conditions without loss of optical quality.

It would be advantageous for silicone materials to be formed using cryogenic lathing procedures, but to date, silicone materials do not possess sufficiently high $T_g$s suitable for cryolathing. The inventors surprisingly found that silicone materials made according to the present description can in certain embodiments possess high enough $T_g$s, remain sufficiently soft and contain a leachable content low enough that extraction does not lead to optical deformation of the silicone materials.

Methods of making silicone materials are within the scope of the present description. Silicone materials can be formed using the components and theories described supra. In one embodiment, a method of forming a silicone material comprises the steps of: a) providing a silicone fluid having a general structure of formula 1

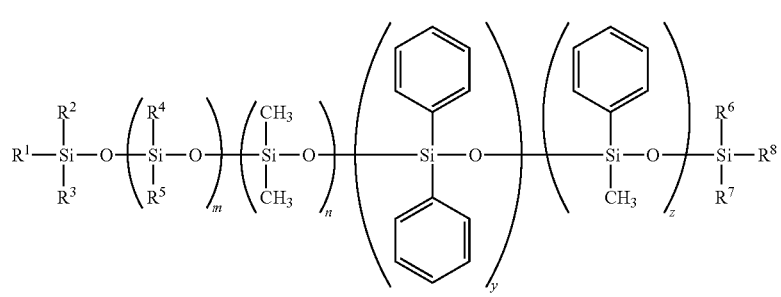

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$; and wherein at least one of, $R^2$, $R^3$, $R^6$, $R^7$, or $R^8$ is $CH=CH_2$; b) providing a cross-linker mixture; c) providing a catalyst; d) combining the silicone fluid, the cross-linker mixture and the catalyst thereby forming a silicone mixture; e) curing said silicone mixture to form an optic material; and f) extracting said optic material to attain an extracted optic material having a total leachable content of less than about 20% and a $T_g$ greater than about −70° C.

The silicone materials once formed can be molded into an appropriate shape. In one embodiment, the shape is a disc that will be formed into a lens. In one embodiment, a disc can be cryogenically lathed into a lens as described supra.

The silicone materials can be extracted at any point in the formation. In one embodiment, the silicone material is extracted before being molded. In another embodiment, the silicone material is extracted after being molded. In another embodiment, the silicone material is extracted both before and after being molded. The silicone materials can undergo several extraction and re-molding steps in order to attain an acceptable leachable content while preserving optical quality.

In one exemplary embodiment, the silicone materials are extracted before cryogenic lathing. As a result of the low level of leachable material in the silicon materials of some embodiments described herein, optical quality is not lost upon extraction. Therefore, there is not a need for multiple extraction and re-processing steps as with common silicon materials. This can be highly advantageous.

The following examples demonstrate that silicone materials can be formed with high and low $T_g$s, varying degrees of polymerization, varying optical properties, to name a few. These examples are intended as exemplary embodiments and are not intended as limitations.

Example 1

Preparation of Polymers

A. Synthesis of a Hexavinyl Terminated Silicone Fluid without Pendent Vinyl Groups.

In a method for making this polymer (polymer B38), 103.48 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 691.78 grams of octamethylcyclotetrasiloxane and 5.15 grams of hexavinyl dislioxane were added together to the reaction kettle. Then, 3.17 grams of tetramethylammonium siloxanolate was added to the reaction kettle. Stirring continued for at least 68 hours at 105° C. (±10° C.). The temperature of the kettle was then raised to 150° C. (±20° C.) for at least 5 hours. After cooling, the silicone fluid was filtered through a 0.2 micron filter.

B. Synthesis of a Hexavinyl Terminated Silicone Fluid with Pendent Vinyl Groups.

In a method for making this polymer (polymer B37), 129.35 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 666.32 grams of octamethylcyclotetrasiloxane, 59.72 grams of tetravinyltetramethylcyclotetrasiloxane and 5.53 grams of hexavinyl dislioxane were added together to the reaction kettle. Then, 4.54 grams of tetramethylammonium siloxanolate was added to the reaction kettle. Stirring continued for at least 25 hours at 105° C. (±10° C.). The temperature of the kettle was then raised to 150° C. (±20° C.) for at least 5 hours. After cooling, the silicone fluid was filtered through a 0.2 micron filter.

C. Synthesis of a High Refractive Index Hexavinyl Terminated Silicone Fluid.

In a method for making this polymer (polymer B29), 249.63 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 546.57 grams of octamethylcyclotetrasiloxane and 5.07 grams of hexavinyl dislioxane were added together to the reaction kettle. Then, 3.36 grams of tetramethylammonium siloxanolate was added to the reaction kettle. Stirring continued for at least 72 hours at 105° C. (±10° C.). The temperature of the kettle was then raised to 150° C. (±20° C.) for at least 5 hours. After cooling, the silicone fluid was filtered through a 0.2 micron filter.

D. Synthesis of a High Refractive Index, High Viscosity Hexavinyl Terminated Silicone Fluid.

In a method for making this polymer (polymer B49), 266.48 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 530.65 grams of octamethylcyclotetrasiloxane and 2.56 grams of hexavinyl dislioxane were added together to the reaction kettle. Then, 3.89 grams of tetramethylammonium siloxanolate was added to the reaction kettle. Stirring continued for at least 18 hours at 105° C. (±10° C.). The temperature of the kettle was then raised to 150° C. (±20° C.) for at least 5 hours. After cooling, the silicone fluid was filtered through a 0.2 micron filter.

A Pope 2" Wiped-Film stills unit was used to remove the volatile components of the above silicone fluids (B38, B37, B29, and B49) by setting the chiller temperature to 5° C., still body temperature to 160° C., the vacuum range to 0.3-2.0 torr and the rotor speed in the range of about 50 to about 70 RPM. A total of about 10% to about 25% of the volatile components were removed from the silicone fluids.

Next, 0.125 grams of 2-(3'-t-butyl-2'-hydroxy-5'-vinyl-phenyl)-5-chlorobenzotriazole (UVAM) was added to 50 grams of each of the above silicone fluids. After centrifugal mixing, the fluids were placed in the 60° C. oven for 2 to 3 days until the UVAM was completely dissolved in the silicone fluids to make "0.25% UVAM silicone fluids."

Example 2

Preparation of Disc 1

In a vessel, 0.045 grams of platinum-cyclovinylmethylsiloxane complex, was added to 15 grams of the B38 0.25% UVAM silicone fluid. The mixture was well mixed by high speed centrifugation at least twice for 30 seconds. The resulting formed "Part A" of the silicone fluid. The final catalyst concentration of three otherwise identical silicone fluids was, by weight, about 0.1%, to about 0.5%. In a separate vessel, "Part B" of the silicone fluid was prepared by mixing 0.4038 grams of 25-30% methylhydrosiloxane-dimethylsiloxane copolymer, trimethylsiloxane terminated (HMS-301 from Gelest) with 5 grams of the B38 0.25% UVAM silicone fluid prepared above. Five grams of Part A and 5 grams of Part B were mixed in a vessel with a theoretical HN ratio=1.0.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 40 kPa and after one day static extraction with IPA, the modulus was 49 kPa. Refractive indices, measured at 19.5° C. (±1° C.), of the disks before and after extraction were 1.434 and 1.433 respectively.

Example 3

Preparation of Disc 2

In a vessel, 0.045 grams of platinum-cyclovinylmethylsiloxane complex, was added to 15 grams of the B38 0.25% UVAM silicone fluid. The mixture was well mixed by high speed centrifugation at least twice for 30 seconds. In a separate vessel, "Part B" of the silicone fluid was prepared by mixing 0.0908 grams of phenyltris(dimethylsiloxy)silane and 5 grams of B38 0.25% UVAM silicone fluid. Five grams of Part A and 5 grams of Part B were mixed in a vessel with a theoretical HN ratio=0.5.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 18 kPa and after one day static extraction with IPA, the modulus was 20 kPa. Refractive indices of the discs before and after extraction were 1.435 and 1.433 respectively.

Example 4

Preparation of Disc 3

A silicone fluid with a high refractive index was prepared according to the following. Part A was prepared by adding 0.045 grams of platinum cyclovinylmethylsiloxane complex to 15 grams of B29 silicone fluid with 0.25% UVAM. Part B was prepared by adding 1.0919 grams of hydride terminated polydimethylsiloxane (DMS-H03 from Gelest) to 15 grams of B29 silicone fluid. Five grams of both Part A and Part B were added to a vessel and mixed with a theoretical HN ratio=1.0.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 47 kPa and after one day static extraction with IPA, the modulus was 54 kPa. Two disks of each were also placed in a soxhlet extraction unit and extracted with IPA for an extended period of time. After extracting for 1, 3, and 5 days, moduli of these samples were 56, 54 and 51 kPa respectively. Refractive index of the discs before extraction was 1.466. Refractive index was 1.465 after one and three days of soxhlet extraction and 1.464 after 5 days of soxhlet extraction.

Example 5

Preparation of Disc 4

A silicone fluid was prepared according to the following. Part A was prepared with B49 0.25% UVAM silicone fluid and 0.1% platinum cyclovinylmethylsiloxane complex. Part B was prepared by adding 0.4294 grams of hydride terminated polydimethylsiloxane (DMS-H03 from Gelest) to 10 grams of B49 silicone fluid. Five grams of both Part A and Part B were added to a vessel and mixed with a theoretical HN ratio=1.2.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 36 kPa and after one day static extraction with IPA, the modulus was 44 kPa. Pot life of the fluid was 6 hours. Refractive indices of the discs before and after static extraction were 1.471 and 1.470 respectively.

Example 6

Preparation of Disc 5

A silicone fluid was prepared with high refractive index and high viscosity silicone fluid. Part A was prepared with 0.25% UVAM B49 silicone fluid and 0.1% platinum carbonyl cyclovinylmethylsiloxane complex. Part B was prepared by adding 0.4294 grams of hydride terminated polydimethylsiloxane (DMS-H03 from Gelest) to 10 grams of B49 silicone fluid. Five grams of both Part A and Part B were added to a vessel and mixed with a theoretical HN ratio=1.2.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 24 kPa and after one day static extraction with IPA, the modulus was 43 kPa. Pot life of the fluid was 20+ hours. The extended pot life would provide flexibility in the manufacturing process.

Example 7

Preparation of Silicone Fluid with Greater than Three but Less than Four Vinyl Terminations This example describes the synthesis of a silicone fluid with an average of 3.74 vinyl terminations. The silicone fluid is prepared by placing 332.03 grams of octaphenylcyclotertasiloxane in a preheated 1000 mL reaction kettle at 105° C. (±10° C.) and stirring. Then, the system is purged with nitrogen for 30 min. After the system is purged, into the reaction kettle is charged 659.60 grams of octamethylcyclotetrsiloxane, 1.75 grams of hexavinyl disiloxane, and 1.80 grams of 1,3-divinyltetramethyl disiloxane. Then, 2.73 grams of tetramethylammonium siloxanolate are added to the reaction mixture. The mixture is kept stirring for at least 20 hours at 105° C. (±10° C.). Then, the temperature of the kettle is raised to 150° C. (±20° C.) for at least five hours. The product of the reaction is then allowed to cool to room temperature. After cooling, the silicone fluid is filtered through a 0.5μ filter and then wiped dry. The resulting silicone fluid has an average of 3.74 vinyl terminations and may have a refractive index of about 1.47.

Example 8

Preparation of Silicone Fluid with Four Vinyl Terminations

A silicone fluid with the average of 4 vinyl terminated groups may be prepared by charging 332.06 grams of octaphenylcyclotetrasiloxane, 659.65 grams of octamethylcyclotetrasiloxane, 2.08 grams of hexavinyl disiloxane, and 1.65 grams of 1,3 divinyltetramethyl disiloxane into a reaction kettle. Then 2.50 grams of tetramethylammonium siloxanolate is added to the kettle and the reaction mixture is kept stirring for at least 20 hours at 105° C. (±10° C.). Then, the temperature of kettle is raised to 150° C. (±20° C.) for at least 5 hours. After cooling, the silicone fluid is filtered through 0.5μ filter before wiped-film process. The resulting silicone fluid has a refractive index of about 1.47.

The following non-limiting examples describe exemplary silicone materials which may be suitable for cryogenic lathing procedures or manufacturing, if such a method or product is desired.

Example 9

Preparation of Silicone Fluid with High Refractive Index

A high refractive index (RI=1.523), high viscosity, hexavinyl terminated silicone fluid was prepared as follows. To a 1000 mL preheated reaction kettle was charged 457.03 grams of octaphenylcyclotetrasiloxane at 105° C. (±10° C.). After turning on the mechanical stirrer, the whole system was purged with nitrogen for at least 30 minutes. Then, 340.84 grams of octamethylcyclotetra-siloxane and 2.15 grams of hexavinyl disiloxane were added to the kettle. Then, 7.35 grams of tetramethylammonium siloxanolate were added initially to the kettle and the reaction mixture was kept stirring for at least 3 hours at 105° C. (±10° C.). Then, an additional 2.04 grams of tetramethylammonium siloxanolate were added to the mixture and the mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The viscosity of this fluid was around 78,000 cp and the refractive index was 1.523.

Example 10

Preparation of Silicone Fluid with a Low Degree of Polymerization

A hexavinyl terminated silicone fluid was prepared as follows. To a 1000 mL preheated reaction kettle was charged 259.77 grams of octaphenylcyclotetrasiloxane at 105° C. (±10° C.). After turning on the mechanical stirrer, the whole system was purged with nitrogen for at least 30 minutes. Then, 199.23 grams of octamethylcyclotetrasiloxane and 46.4 grams of hexavinyl disiloxane were added to the kettle. Then, 3.06 grams of tetramethylammonium siloxanolate were added initially to the kettle and the reaction mixture was kept stirring for at least 3 hours at 105° C. (±10° C.). Then, an additional 2.47 grams of tetramethylammonium siloxanolate were added to the mixture, then another 1.50 grams, and then the mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.52. The sum of x, y and z (equal to the degree of polymerization) was about 22. This silicon fluid can be useful in formulating, for example, but not limited to, contact lens solutions and hair sprays.

Example 11

Preparation of Silicone Fluid with a Low Degree of Polymerization

A hexavinyl terminated silicone fluid was prepared as follows. To a 1000 mL preheated reaction kettle was charged 250.26 grams of octaphenylcyclotetrasiloxane at 105° C. (±10° C.). After turning on the mechanical stirrer, the whole system was purged with nitrogen for at least 30 minutes. Then, 181.87 grams of octamethylcyclotetrasiloxane and 18.08 grams of hexavinyl disiloxane were added to the kettle. Then, 2.70 grams of tetramethylammonium siloxanolate were added to the kettle and the reaction mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.53. The sum of x, y and z was equal to about 50. This silicon fluid can be useful in formulating, for example, but not limited to, contact lens solutions and hair sprays.

Example 12

Preparation of Silicone fluid with a Medium Degree of Polymerization

A hexavinyl terminated silicone fluid was prepared as follows. To a 1000 mL preheated reaction kettle was charged 109.05 grams of octaphenylcyclotetrasiloxane at 105° C. (±10° C.). After turning on the mechanical stirrer, the whole system was purged with nitrogen for at least 30 minutes. Then, 236.05 grams of octamethylcyclotetrasiloxane and 3.56 grams of hexavinyl disiloxane were added to the kettle. Then, 2.00 grams of tetramethylammonium siloxanolate were added to the kettle and the reaction mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.46. The sum of x, y and z was equal to about 248. This silicon fluid can be useful in formulating, for example, but not limited to, topical skin compositions such as skin creams and lotions.

Example 13

Preparation of Silicone Fluid with an Increased $T_g$

A silicone fluid (B54) with a relatively high $T_g$ was prepared as follows. To a 1000 mL preheated reaction kettle was charged 571.30 grams of octaphenylcyclotetrasiloxane at 105° C. (±10° C.). After turning on the mechanical stirrer, the whole system was purged with nitrogen for at least 30 minutes. Then, 425.84 grams of octamethylcyclotetra-siloxane and 3.39 grams of hexavinyl disiloxane were added to the kettle. Then, 5.56 grams of tetramethylammonium siloxanolate (N-Cat) were added to the kettle and the reaction mixture was kept stirring for at least 48 hours at 105° C. (±10° C.). The temperature of kettle was raised to 150° C. (±20° C.) for at least 5 hours. After cooling, the silicone fluid was filtered through 0.2μ filter before a solvent extraction process. The refractive index was 1.523 at 22° C. The $T_g$ of the silicone fluid was −56° C.

Example 14

Preparation of Silicone Fluid with an Increased $T_g$

A silicone fluid (B55) with a decreased relative viscosity was prepared as follows. The viscosity of the silicon fluid prepared in Example 13 was prepared by adding additional hexavinyl disiloxane during the formation process as follows. To a 1000 mL preheated reaction kettle was charged 571.18 grams of octaphenylcyclotetrasiloxane at 105° C. (±10° C.). After turning on the mechanical stirrer, the whole system was purged with nitrogen for at least 30 minutes. Then, 423.88 grams of octamethylcyclotetra-siloxane and 5.06 grams of hexavinyl disiloxane were added to the kettle. Then, 4.49 grams of tetramethylammonium siloxanolate (N-Cat) were added to the kettle and the reaction mixture was kept stirring for at least 48 hours at 105° C. (±10° C.). The temperature of kettle was raised to 150° C. (±20° C.) for at least 5 hours. After cooling, the silicone fluid was filtered through 0.2μ filter before a solvent extraction process. The refractive index was 1.524 at 22° C.

Example 15

Preparation of Silicone Fluid with an Increased $T_g$ and Pendent Vinyl Groups

A silicone fluid (B56) with pendent vinyl groups was prepared as follows. To a 1000 mL preheated reaction kettle was charged 571.32 grams of octaphenylcyclotetrasiloxane at 105° C. (±10° C.). After turning on the mechanical stirrer, the whole system was purged with nitrogen for at least 30 minutes. Then, 402.72 grams of octamethylcyclotetrasiloxane, 24.63 grams of tetravinyltetramethylcyclotetrasiloxane and 5.07 grams of hexavinyl disiloxane were added to the kettle. Then, 2.72 grams of tetramethylammonium siloxanolate (N-Cat) were added to the kettle and the reaction mixture was kept stirring for at least 25 hours at 105° C. (±10° C.). The temperature of kettle was raised to 150° C. (±20° C.) for at least 5 hours. After cooling, the silicone fluid was filtered through 0.2μ filter before a solvent extraction process. The refractive index was 1.524 at 23.8° C.

Example 16

Solvent Extraction from Silicone Fluid

The silicone fluid from Example 13 (B54) was treated by solvent extraction to remove the unreacted/undesired oligimers in the silicone fluid. A clean glass jar was charged with 200 grams of a silicone fluid from Example 13 (B54) and slow addition of 200 grams of isopropyl alcohol (IPA). Moderate agitation was used during the addition of the IPA. After 5 minutes of moderate agitation, the mixture was allowed to sit for about 1-2 minutes. The top IPA layer was carefully decanted off and an additional 200 grams of IPA was added to the jar, again with moderate agitation. After settlement, the IPA was again decanted off. The above washing process was repeated an additional three times (for a total of five washes). The glass jar was charged with a small amount of IPA (~10 grams) and placed in a oven at 100° C. for 24 hours to remove as much IPA as possible. Finally, the glass jar was placed in a vacuum oven at 90° C. to remove any trace amounts of IPA that still remain sequestered in the silicon fluid. A glass rod was used to agitate the silicon fluid every 2 hours and the silicon fluid was weight each time until a constant weight is obtained. The typical yield of the silicon fluid from Example 13 (B54) by this process is about 84%.

Example 16

Preparing a Silicone Disc or Slab

A disk or slab of silicone fluid(s) can be prepared as follows. A centrifuge cup is charged with 0.025 grams of platinum carbonyl cyclovinylmethylsiloxane complex along with about 10 grams of silicon fluid from Example 15 (B54M). The mixture is mixed well using centrifugal force. The mixture is labeled "part A."

A separate centrifuge cup is charged with 0.1523 grams of phenyl crosslinker (XL-106 from Nusil), 0.209 grams of hydride Q resin (HQM-107 from Gelest) and 0.086 grams monohydride terminated polydimethylsiloxane (MCR-H07 from Gelest). This mixture is labeled "part B." About 10 grams of "part A" is mixed with "part B" and mixed well. Equal amounts of "part A" and "part B" were mixed together by centrifugal force and poured into a Teflon® mold. After the Teflon® mold has been filled with the mixture, it was placed in an oven at 140° C. for 10 minutes. After 10 minutes, the mold was removed from the oven and the disc was removed from the mold.

A slab of silicon fluid can be produced by mixing "part A" and "part B" as described above. The mixture is poured into a tray forming a slab of the mixture. The tray is placed in an oven at 140° C. for 10 minutes. After 10 minutes, the tray is removed from the oven and the slab is removed from the tray. The slab can be cut using a tool such as a punch to generate several discs from a single slab.

The above formulation can be prepared in by different methods. For example, the hydride mixtures can be placed in the centrifuge cup first, then the silicone fluid can be added on top of the hydride mixture, finally a suitable amount of platinum carbonyl cyclovinylmethylsiloxane complex can be added to the cup and all components mixed in the centrifugal force. Compression moduli prepared by different methods are similar assuming the ratio of each component is the same. This formulation is designated as B54M8:1:1 and can be used to prepare optics in the accommodating IOL.

Example 17

Modulus Measurement of Silicone Disc

The modulus of discs as produced in Example 16 can be measured by the following method. The modulus of the discs was measured using a Q800 DMA (TA 687+ruments). The diameter and thickness of the disc was measured using an optical comparator. After loading the disc on the holder, the temperature of the system was rasied to 35° C. and allowed to come to equilibrium for 5 minutes. After at least 5 minutes at equilibrium, a ramp force was applied to the disc a 1 N/min to a maximum of 9 N. The modulus was determined by the slope of the two elongation points (4% and 8%) from the curve. The modulus of a disc comprising non-extracted silicone fluid from Example 13 was 63 kPa. If the same silicone fluid from Example 13 was subjected to five days of soxhlet extraction with IPA, the modulus of such a disc was 91 kPa.

Example 18

Preparation of a Silicone Material with a Higher Degree of Rigidity

This example illustrates how to prepare a silicone material with a higher degree of rigidity. A centrifuge cup was charged with 0.1355 grams of hydride terminated polyphenyl-(dimethylhydrosiloxy)siloxanes (HDP-111) and 0.029 grams of hydride Q resin (HQM-107). Then, 9.83 grams of solvent extracted silicone fluid from Example 15 was poured into the cup. Finally, 0.0125 grams of platinum carbonyl cyclovinylmethylsiloxane complex was added to the cup. After mixing the contents of the cup by centrifugal force, this mixture was used to prepare discs as described in Example 16. The modulus of the discs was determined by the method of Example 17 to be 188 kPa. A material such as this would be ideal for forming haptics.

Example 19

Preparation of a Second Silicone Material with a Higher Degree of Rigidity

This example illustrates how to prepare a different silicone material with a higher degree of rigidity. A centrifuge cup was charged with 0.1142 grams of phenyl crosslinker (XL-106) and 0.0314 grams of hydride Q resin (HQM-107). Then, 9.84 grams of silicone fluid of Example 14 extracted by the methods of Example 15 was added to the cup. Finally, 0.0125 grams of platinum carbonyl cyclovinylmethylsiloxane complex was added to the cup. After mixing the contents of the cup by centrifugal force, this mixture was used to prepare discs as described in Example 16. The modulus of the discs was determined by the method of Example 17 to be 327 kPa. A material such as this would be ideal for forming haptics.

Example 20

Preparation of an accommodating IOL by Injection Molding

An accommodating IOL can be made according to the following method. Haptics of diameter 9.6 mm made of commercially available materials such as MED6820 or MED6750 were prepared by injection molding. Silicone discs from Example 16 were used to over-mold on top of the haptics to make a final lens. Additional lenses were made using silicone discs of Example 16 which had been subjected to soxhlet extraction for 5 days. The results are summarized in Table 1.

TABLE 1

| | Resolution Efficiency in Water | | | |
|---|---|---|---|---|
| | 9.6 mm MED 6750 haptic | | 9.6 mm MED 6820 haptic | |
| IOL Number | Before Extraction | After Extraction | Before Extraction | After Extraction |
| 1 | 3-6 | 4-1 | 3-4 | 3-5 |
| 2 | 3-6 | 4-1 | 3-4 | 3-6 |
| 3 | 4-2 | 3-4 | 3-5 | 3-5 |

It is clear from the results in Table 1 that the resolution of the silicone lens material does not deteriorate due to solvent extraction, even after 5 days of soxhlet extraction with IPA.

Example 21

Preparation of an accommodating IOL by Compression Molding

An accommodating IOL can be made according to the following method. Haptics of diameter 9.6 made of commercially available materials such as MED6820 were prepared by compression molding. Silicone discs from Example 16 were used to over-mold on top of the haptics to make a final lens. Additional lenses were made using silicone discs of Example 16 which had been subjected to soxhlet extraction for 5 days. The results are summarized in Table 2.

TABLE 2

| | Resolution Efficiency in Water | |
|---|---|---|
| IOL Number | Before Soxhlet Extraction | After Soxhlet Extraction |
| 1 | 4-2 | Save for control |
| 2 | 4-2 | 4-2 |
| 3 | 4-2 | 3-6 |
| 4 | 4-2 | 4-2 |

It is clear from the results in Table 2 that the resolution of the silicone lens material does not deteriorate due to solvent extraction, even after 5 days of soxhlet extraction with IPA.

Example 22

A Second Preparation of an accommodating IOL by Compression Molding

An accommodating IOL can be made according to the following method with haptic material from Example 18. The silicone fluid optic material is made according to Example 16. An accommodating IOL is made of the above components. A resolution in water is measured of the completed lens and is 3-6. The lens is subjected to 5 days of soxhlet extraction with IPA after which the resolution in water is measured to be 4-4. Table 2 illustrates that the resolution of the silicone lens material does not deteriorate due to solvent extraction, even after 5 days of soxhlet extraction with IPA.

Example 23

Formation of an IOL Using Cryogenic Lathing

Different IOL discs were made according to the methods of Example 6. One disc was made using the silicone fluid of Example 15 and another disc was made of MED6820 silicone. The silicone disc made by the methods of Example 15 had a $T_g$ of about −56° C. and the MED6820 silicon disc had a $T_g$ of about −109° C. With a $T_g$ of −106° C., the MED6820 silicone disc did not have the properties allowing it to be lathed at cryogenic temperatures. The disc made according to the methods of Example 15 had a $T_g$ high enough to allow for lathing at cryogenic temperatures which in turn allows for the manufacture of a more defect free lens.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A silicone material formed from a silicone fluid, at least one cross-linker, and at least one monofunctional hydride compound, wherein the silicone fluid has a general structure of formula 1

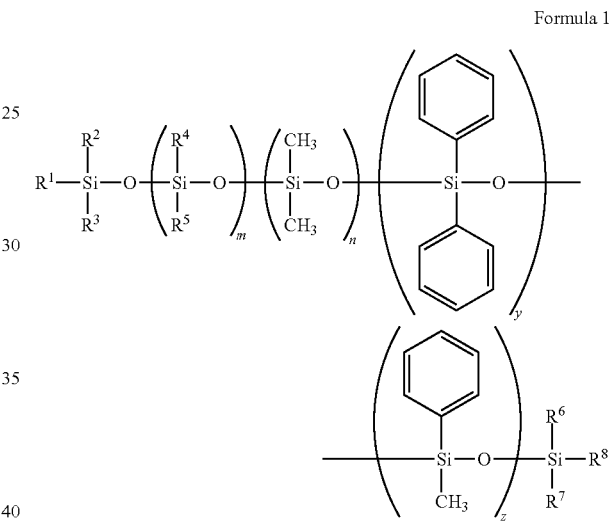

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH{=}CH_2$, if m is greater than zero, at least one of $R^4$ or $R^5$ must be $CH{=}CH_2$;

wherein at least one of $R^1$, $R^2$, $R^3$, $R^6$, $R^7$, or $R^8$ is $CH{=}CH_2$; and wherein said silicone material has a $T_g$ greater than $-70°$ C. and contains a total leachable content of less than about 20%.

2. The silicone material according to claim 1 wherein said silicone material has a compression modulus less than about 200 kPa.

3. The silicone material according to claim 1 wherein said silicone material has a compression modulus less than about 100 kPa.

4. The optic material according to claim 1 wherein said material has refractive index of less than about 1.55.

5. A lens comprising a cured polymeric material with a general structure of formula 1

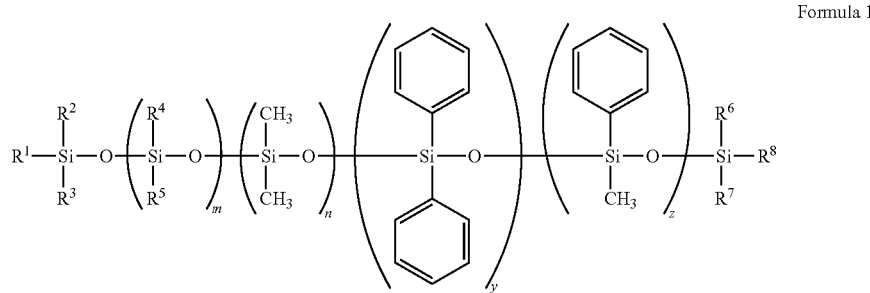

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$;

wherein at least one of $R^1$, $R^2$, $R^3$, $R^6$, $R^7$, or $R^8$ is $CH=CH_2$;

wherein said cured polymeric material further comprises a cross-linker and a monofunctional hydride compound; and wherein said lens has a $T_g$ greater than −70° C. and contains a total leachable content of less than about 20%.

6. The lens according to claim 5 wherein said lens has a compression modulus less than about 200 kPa.

7. The lens according to claim 5 wherein said lens has a compression modulus less than about 100 kPa.

8. The lens according to claim 5 wherein said lens has a refractive index of less than about 1.55.

9. The lens according to claim 5 wherein said lens is an ocular lens selected from the group consisting of in intraocular lens and a contact lens.

10. A method of forming at least a portion of a silicon lens comprising the steps of:
(a) providing silicone fluid of a general structure of formula 1 wherein at least one of $R^1$, $R^2$, $R^3$, $R^6$, $R^7$, or $R^8$ is $CH=CH_2$;
b) providing a cross-linker mixture;
c) providing a catalyst;
d) combining the silicone fluid, the cross-linker mixture and the catalyst thereby forming a polymer mixture;
(e) setting up a mold with said polymer mixture thereby forming a molded optic material;
(f) curing said molded optical material thereby forming a cured optic material, wherein said cured optic material has a $T_g$ greater than −70° C.; and
(g) cryolathing said cured optic material to form a portion of a silicone lens.

11. The method according to claim 10 wherein the optic material is extracted prior to step (g), thereby attaining a polymer with a total leachable content of less than about 20%.

12. The method according to claim 10 wherein said lens has a compression modulus less than about 200 kPa.

13. The method according to claim 10 wherein said lens has a compression modulus less than about 100 kPa.

14. The method according to claim 10 wherein said lens has a refractive index of less than about 1.55.

15. The method according to claim 10 wherein said lens is an ocular lens selected from the group consisting of in intraocular lens and a contact lens.

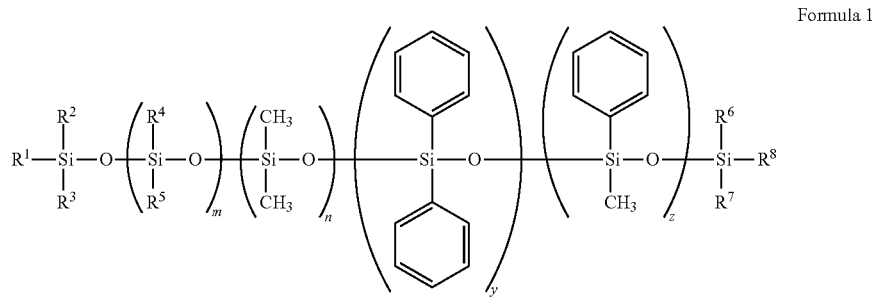

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$;

16. The method according to claim 10 wherein said cross-linker mixture comprises a monofunctional hydride compound.

17. A method of forming an optic lens comprising the steps of
a) providing silicone fluid having a general structure of formula 1

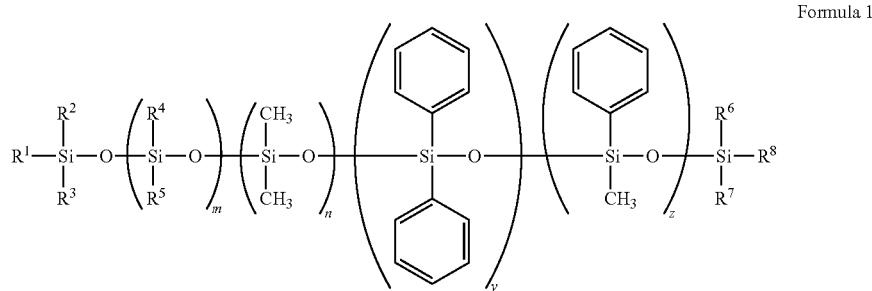

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$;

wherein at least one of $R^2$, $R^3$, $R^6$, $R^7$, or $R^8$ is $CH=CH_2$;

b) providing a cross-linker mixture; wherein said cross-linker mixture contains a cross-linker and a monofunctional hydride compound;

c) providing a catalyst;

d) combining the silicone fluid, the cross-linker mixture and the catalyst thereby forming a silicone mixture;

e) curing said silicone mixture to form an optic lens; and f) extracting said optic lens to attain an extracted optic lens having a total leachable content of less than about 20% and a $T_g$ greater than about −70° C.

18. The method according to claim 10 wherein the polymer mixture is extracted prior to step (e).

19. A method of forming at least a portion of a lens comprising the steps of:

a) providing silicone fluid of a general structure of formula 1 between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$;

wherein at least one of $R^1$, $R^2$, $R^3$, $R^6$, $R^7$, or $R^8$ is $CH=CH_2$;

b) providing a cross-linker mixture comprising a monofunctional hydride compound;

c) providing a catalyst;

d) combining the silicone fluid, the cross-linker mixture and the catalyst thereby forming a polymer mixture;

(e) setting up a mold with said polymer mixture thereby forming a molded optic material;

(f) curing said molded optic material thereby forming a cured optic material, wherein said cured optic material has a $T_g$ greater than about −70° C.; and (g) cryolathing said cured optic material to form a lens.

20. A method of forming at least a portion of a lens consisting essentially of the steps of:

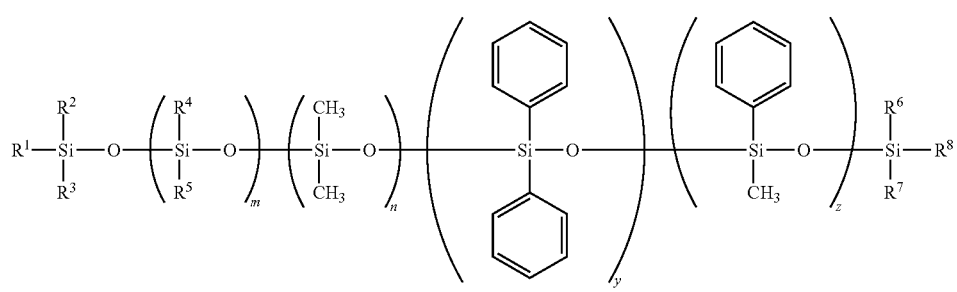

Formula 1 wherein the sum of m and n is x, x is between about 0 to about 12000, y is between about 0 to about 500, and z is a) providing silicone fluid of a general structure of formula 1

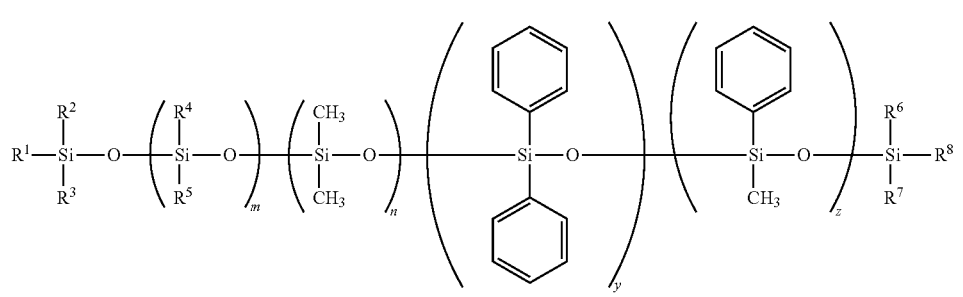

Formula 1 wherein the sum of m and n is x, x is between about 0 to about 12000, y is between about 0 to about 500, and z is between about 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$;

wherein at least one of $R^1$, $R^2$, $R^3$, $R^6$, $R^7$, or $R^8$ is $CH=CH_2$;

b) providing a cross-linker mixture comprising a monofunctional hydride compound;

c) providing a catalyst;
d) combining the silicone fluid, the cross-linker mixture and the catalyst thereby forming a polymer mixture;
(e) setting up a mold with said polymer mixture thereby forming a molded optic material;
(f) curing said molded optic material thereby forming a cured optic material, wherein said cured optic material has a $T_g$ greater than about −70° C.; and
(g) cryolathing said cured optic material to form a lens.

* * * * *

UNITED STATES PATENT AND TRADEMARK OFFICE
CERTIFICATE OF CORRECTION

| | | |
|---|---|---|
| PATENT NO. | : 8,530,590 B2 | Page 1 of 1 |
| APPLICATION NO. | : 12/205703 | |
| DATED | : September 10, 2013 | |
| INVENTOR(S) | : Can Hu, Derek D. Pham and Michael D. Lowery | |

It is certified that error appears in the above-identified patent and that said Letters Patent is hereby corrected as shown below:

On the title page, Item (73) Assignee should read as: Abbott Medical Optics Inc.

Signed and Sealed this
Twenty-ninth Day of October, 2013

Teresa Stanek Rea
*Deputy Director of the United States Patent and Trademark Office*